(12) United States Patent
Rossi

(10) Patent No.: US 6,598,464 B1
(45) Date of Patent: Jul. 29, 2003

(54) OIL AND CONTAMINANTS ANALYZER

(76) Inventor: Sergio Rossi, 2303 Grimsley Tr., Mansfield, TX (US) 76063

( * ) Notice: Subject to any disclaimer, the term of this patent is extended or adjusted under 35 U.S.C. 154(b) by 0 days.

(21) Appl. No.: 09/676,964

(22) Filed: Oct. 2, 2000

Related U.S. Application Data

(60) Provisional application No. 60/157,416, filed on Oct. 2, 1999.

(51) Int. Cl.$^7$ .................. G01N 33/26; G01N 11/00; G01N 15/02
(52) U.S. Cl. .............. 73/53.05; 73/53.01; 73/53.07; 73/61.91; 73/61.42; 73/61.43; 73/61.52; 73/61.55; 356/70
(58) Field of Search ............. 73/53.01, 53.05, 73/53.07, 61.41, 61.42, 61.71, 61.72, 64.56, 61.43, 61.44, 61.52, 61.54, 61.55; 356/70

(56) References Cited

U.S. PATENT DOCUMENTS

| | | | | | |
|---|---|---|---|---|---|
| 2,889,736 | A | * | 6/1959 | Borg ........................... | 356/70 |
| 3,049,964 | A | * | 8/1962 | Miller et al. .................. | 356/70 |
| 3,182,255 | A | * | 5/1965 | Hopkins et al. ............. | 324/666 |
| 3,526,127 | A | * | 9/1970 | Sarkis ........................ | 73/53.05 |
| 4,047,814 | A | * | 9/1977 | Westcott ..................... | 356/38 |
| 4,082,511 | A | * | 4/1978 | Bedford ....................... | 436/60 |
| 4,169,677 | A | * | 10/1979 | Luria ......................... | 73/53.07 |
| 4,254,656 | A | * | 3/1981 | Sanford et al. ............. | 73/61.52 |
| 4,651,560 | A | * | 3/1987 | Lester et al. .............. | 73/53.07 |
| 4,671,102 | A | * | 6/1987 | Vinegar et al. ............ | 73/61.43 |
| 5,055,202 | A | * | 10/1991 | Carroll et al. ............. | 73/61.44 |
| 5,200,064 | A | * | 4/1993 | Russ et al. ................. | 73/61.71 |
| 5,262,732 | A | * | 11/1993 | Dickert et al. ............. | 324/672 |
| 5,313,824 | A | * | 5/1994 | Herguth et al. ............ | 73/53.05 |
| 5,506,501 | A | * | 4/1996 | Fogel et al. ................ | 324/204 |
| 5,517,427 | A | * | 5/1996 | Joyce ......................... | 73/53.05 |
| 5,540,089 | A | * | 7/1996 | Fitch .......................... | 73/61.42 |
| 5,588,535 | A | * | 12/1996 | Thornton et al. ............ | 209/38 |
| 5,808,180 | A | * | 9/1998 | Roussis et al. ............ | 73/23.35 |
| 5,817,928 | A | * | 10/1998 | Garvey, III et al. ....... | 73/53.05 |
| 5,923,431 | A | * | 7/1999 | Masterson et al. ......... | 356/426 |
| 6,286,363 | B1 | * | 9/2001 | Discenzo ................... | 73/53.01 |

* cited by examiner

*Primary Examiner*—Daniel S. Larkin
*Assistant Examiner*—Michael Cygan

(57) ABSTRACT

A process, a method and apparatus are provided for testing and analyzing oil's physical and chemical characteristics and contaminants found in oil. A process separates contaminants prior to testing of oil's chemical and physical characteristics and includes manufacturing and operation parameters, and visual techniques for analysis. An apparatus is provided to separate and remove contaminants into magnetic, non-magnetic and liquids for further testing and analysis. This is accomplished using magnetic fields, filtration and condensing systems. The testing of oil's chemical and physical characteristics as well as contaminants is done using a plurality of tests such as viscosity, blotter, opacity and images for contaminants. A method is provided to prepare blotter and filtration systems, to remove fluid contaminants from particles and to include process parameters, trending and graphical analysis of images via software programming.

22 Claims, 11 Drawing Sheets

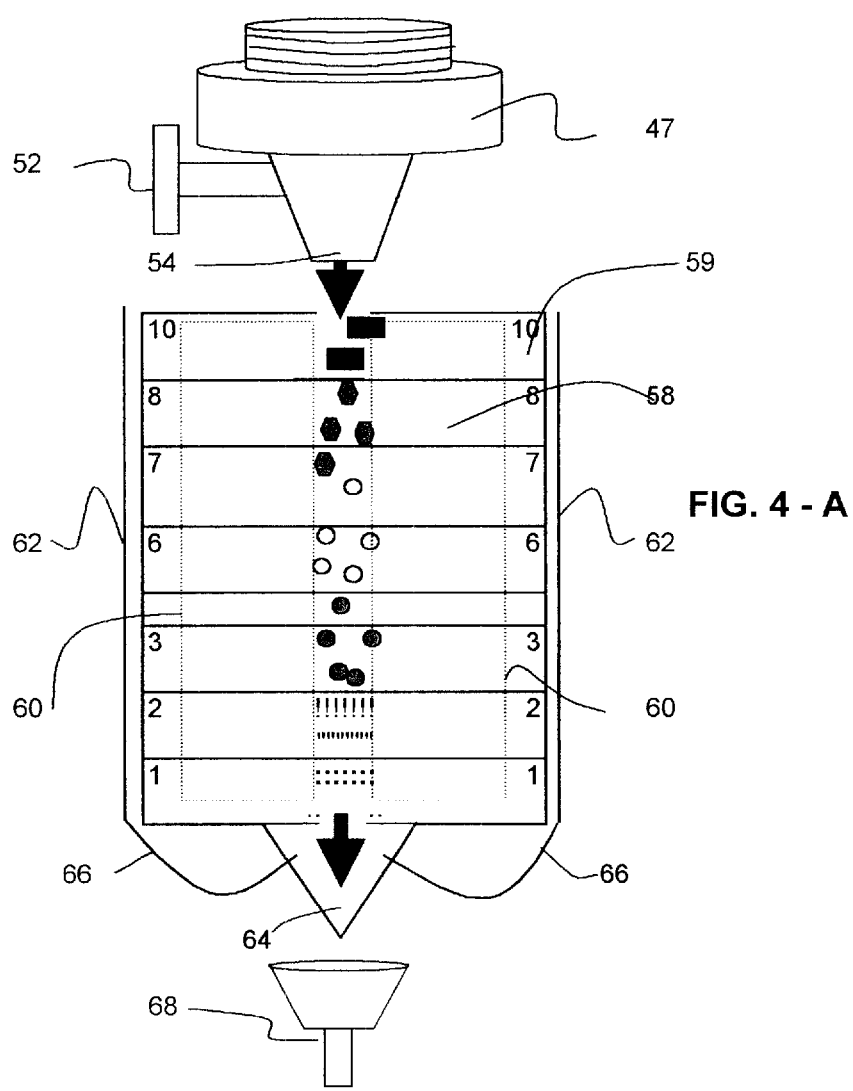
FIG. 4 - A
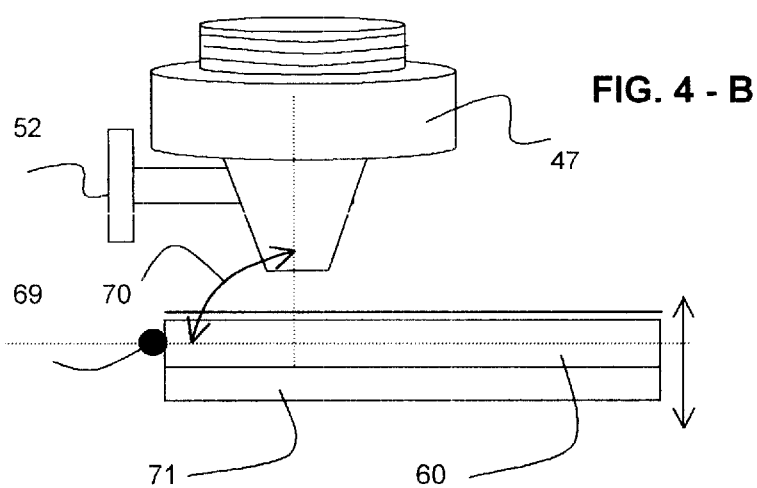
FIG. 4 - B

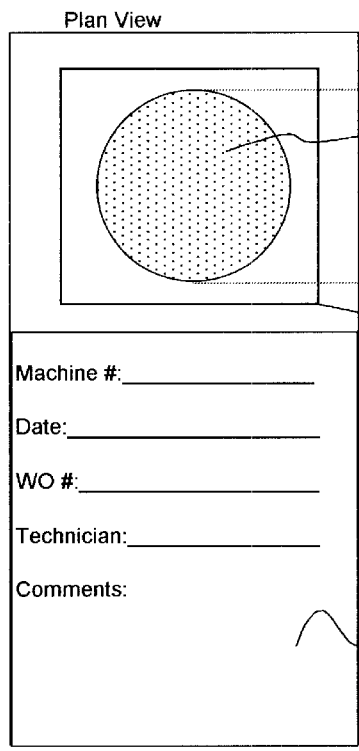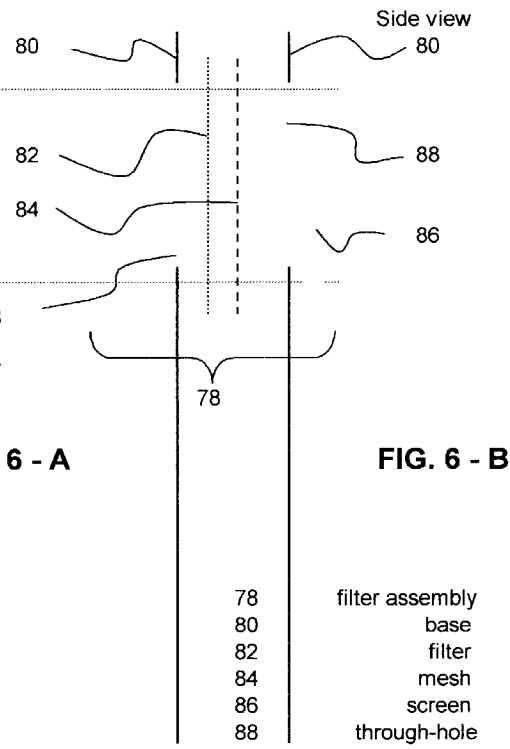
FIG. 6 - A
FIG. 6 - B
| 78 | filter assembly |
| 80 | base |
| 82 | filter |
| 84 | mesh |
| 86 | screen |
| 88 | through-hole |
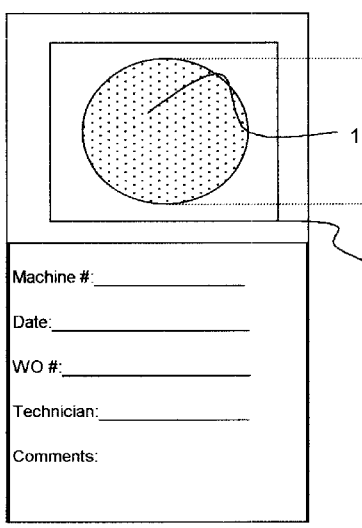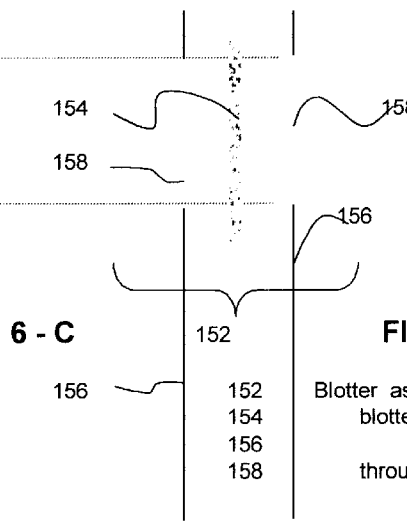
FIG. 6 - C
FIG. 6 - D
| 152 | Blotter assembly |
| 154 | blotter paper |
| 156 | base |
| 158 | through-hole |

| Chemical Trend Analysis | |
|---|---|
| TAN/TBN trend | Machine temp/load/speed |
| 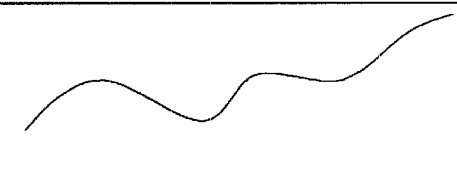 | 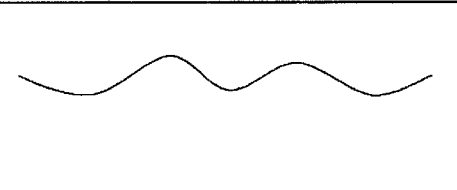 |
| viscosity trend | Data |
| 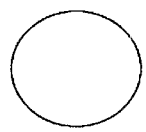 | Water present: TRUE<br>Other fluids: FALSE<br><br>Product: 60-007 clear<br>Sample data: 2/8/99<br>TAN: 0.6   Temperature: 125<br>TBN; 5   Machine Load: 79<br>Viscosity: 35   Machine Speed: 78 |
FIG. 11 - A
| Physical Trends | | | |
|---|---|---|---|
| Blotter Images | | | |
| 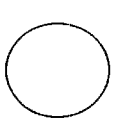 | 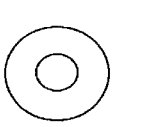 | 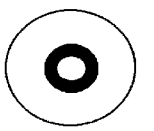 | 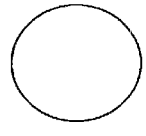 |
| 1/3/99 | 1/8/99 | 1/1/00 | 1/5/00 |
| Opacity Images | | | |
| 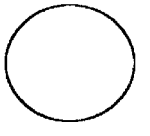 | 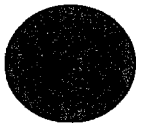 |  | |
| 1/3/99 | 1/8/99 | 1/1/00 | 1/5/00 |
FIG. 11 - B

FIG. 12 - A
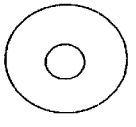
FIG. 12 - B

OIL AND CONTAMINANTS ANALYZER

This application claims the benefit of Provisional application Ser. No. 60/157,416, filed Oct. 2, 1999.

BACKGROUND

1. Field of Invention

The present invention relates to a process, method and apparatus to analyze fluids, specifically to the process, method and apparatus for separating, testing and analyzing oil and its contaminants.

2. Background Discussion of Prior Art

Industrial fluids, in particular organic and synthetic oils, are used to lubricate machinery components such as bearings and gears. The purpose of lubricating those surfaces is to increase component's life by reducing friction and by removing heat generated in the friction area.

Oil's physical characteristics such as color, viscosity and temperature and chemical characteristics such as total acid number (TAN), total base numbers (TBN), oxidation, etc. must be closely monitored in order to achieve longer machinery life. Solid and fluid contaminants should be separated to determine the failing component so that parts and preventative maintenance labor is scheduled to reduce costs.

For such purpose, oil samples should be tested and analyzed to understand its condition and to detect the onset of failure before it occurs. Oil samples should be properly separated, tested and analyzed to fully understand two variables:

a) Solid and fluid contaminants (contaminants)

b) Physical and chemical characteristics of oil (oil characteristics)

These two variables have been partially and individually addressed by a wide variety of methods and instruments, but never adequately combined in a process. These different methods and instruments had and still have significant problems. Test methods and instruments are difficult to use in industrial sites due to the large number and variety of different tests available, testing limitations that each tester has and the difficulty to accurately trend over time parameters that are critical for machine performance and reliability. Current methods do not include a process to separate contaminants prior to testing, which is critical for proper testing of oil physical and chemical characteristics. Current instruments are designed for lab environments and are not portable or rugged. Process parameters such as speed, percent load and product are not included in analysis which severely affects the understanding of the entire system composed of process-machine performance and its lubricants. Visual tests and visual trending are not used to simplify and communicate plant wide test results via software.

Several patents have been issued for oil testing methods and instrumentation. U.S. Pat. No. 2,889,736 to Ed M. Borg (1959) uses a light beam to determine approximate percentage of contaminants, U.S. Pat. No. 3,049,964 uses an optical means to indicate oil conditions, U.S. Pat. Nos. 3,578,865, 3,364,812, 3,731,743, 3,714,444, 3,734,629 all employ light as a source for test one of oils many unknowns. U.S. Pat. No. 3,182,255 to Hopkins (1965) uses a capacitor sensor, U.S. Pat. No. 4,082,511 to Pricon (1978) does TAN and TBN testing, U.S. Pat. No. 4,651,560 uses a filtration method, and many other patents address testing oils partially. U.S. Pat. No. 4,047,814 to Wescott provides a method to determine type, size and distribution of metallic particles, testing oil partially since physical and chemical characteristics are not tested. U.S. Pat. No. 5,506,501 assigned to CSI (1996) prepares samples of oil by separating magnetic and non magnetic particles only testing oils partially. U.S. Pat. No. 5,517,427 to Carlton S. Joyces (1996) uses an infrared spectrometer and an optical emission spectrometer for testing which are large equipment used in lab environments that could not be utilized in harsh industrial environments. U.S. Pat. No. 5,262,732 to Dickert et al. uses a capacitor grid sensor to determine contaminant levels. Magnetic and non magnetic particles are clumped together which makes it hard to perform visual inspection and differentiate among particles. Lightweight process contaminants such as plastic pellets, powders such as flour and condiments tend to stay afloat and never precipate down to the capacitor grid and therefore providing erroneous readings. When contaminants are of small sizes, they tend to remain above and beyond the magnetic field strength taking too long for particles to settle down at the bottom of the capacitor grid. U.S. Pat. No. 5,817,928 to CSI Technology, Inc provides a method for evaluating a multiplicity of lubrication quality parameters that are assigned to categories of wear, chemistry and contaminants. This method provides indices for representing each categories which tends to confuse operators who are not familiar with index numbers and can not be correlated to any other tests or methods. This software doesn't provide a method for including process parameters such as speed, load and product critical to understanding machine performance. It uses a particle counter which provides an index number proportional to ferrous and non-ferrous particles larger than a predetermined minimum and therefore many particles are not counted leading to erroneous results. This method doesn't provide a process to separate particles prior to testing for oil chemistry which leads to erroneous and misleading results. U.S. Pat. No. 5,588,535 to Thornton et al. provides a separation method. Particles are separated as magnetic and non-magnetic and according to sizes but it is done in three different groups which limits trending capabilities of the particles. It prepares the samples for specific lab testers such as energy dispersive x-ray fluorescent EDXRF, machine designed for lab environments. This system does not test for oil's chemical and physical characteristics. U.S. Pat. No. 3,526,127 to Sarkis (1969) tests for viscosity, IR characteristics and metal content of an oil sample, nevertheless it has a severe limitation in the particle detection range between 5–15 microns. This system does not test for oil's chemical and physical characteristics. Kits have been used for testing oil characteristics and contaminants. Commercially available kits such as Kittiwake Developments Ltd. have been available for quite some time. These kits have been used in remote locations such as mining or off-shore oil exploration but have not been widely accepted in the manufacturing industry due to their size, lack of portability or extreme simplicity. They tend to test either particle separation or chemical characteristics of oil. Another test kit introduced in the oil testing is U.S. Pat. No. 5,313,824 by Herguth (1994) whose kit visually analyzes the "deterioration" of oil by using a blotter paper. The resulting blot is visually compared with standard samples that are descriptive of different deterioration levels. This method does not have software that can document, communicate and trend information. This method does not test for physical characteristics of oil or contaminants.

Disadvantages:

1. Oil analysis is done to determine the chemical and physical conditions of oil and to determine the presence and the origins of contaminant particles. The chemical and physical conditions are needed to change the oil at the right time, before it stops reducing friction. The origin of contaminants is needed to determine which is the failing component that needs to be replaced. None of the prior art references uncovered in the search shows a process for separating of contaminants to isolate contaminant origins prior to the testing and analysis of the chemical and physical characteristics of industrial oils. Current testing techniques simultaneously test for both oil condition and contaminants without separation of contaminants prior to testing of oil characteristics. This creates three main problems. 1) Testing results measuring a combination of particles and contaminants without understanding particle's origin defeats the purpose of the analysis. This, in addition, leads to confusing and costly results since an entire system may be replaced where only one part may be failing and may need replacing. 2) Some testing methods are affected significantly by the lack of separation. For example, particle counters provide a result indicating a number of particles found in a sample of oil within a certain size range, but since they haven't been separated, no one can determine if their origin is the production process or the machine. Air bubbles are trapped in the oil sample and produce misleading results when using laser type particle counters. 3) The third main problem created is that contaminants may significantly alter the chemical and physical characteristics of the oil. Oil saturated with production contaminants such as powders will alter the viscosity readings significantly. Capacitance testing of a sample that still contains metal contaminants will show a different capacitance than if the sample did not have any contaminants. Another physical characteristic that may be affected by not separating contaminants prior to testing for chemical or physical characteristics of oil is opacity. If water in its emulsified state is present in the oil sample, it will show a different opacity level than if not present. The instrument for separating of contaminants for properly testing and analyzing oil characteristics is not currently available and it is needed.

2. The separation of contaminants to test chemical and physical characteristics of oils should be done in an orderly manner and following a process. A process for separating of contaminants for properly testing and analyzing chemical and physical characteristics of industrial oils and their contaminants is not currently available and it is very needed.

3. Current test methods and instruments are not built for industry and are difficult to use and understand for industrial operators not trained for lab environments. Originally, oil samples were sent to an external lab for a detailed analysis. Therefore, instruments for testing oils have been designed and built for a very clean, dust-free and climate-controlled environment. These conditions are not typically found in the industry rendering these instruments useless in environmental conditions with high heat, dust and humidity commonly found in manufacturing plants. Test equipment such as infrared spectrometry, optical emission spectrometry, x-ray fluorescence and others, are complex and difficult to use for those untrained in the field of chemistry or physics. In addition, since labs process hundreds of oil samples per day, instruments were made automated to satisfy the demand for high speed testing and quick report turn around. These requirements make them very expensive, large and sophisticated. (Only 5 to 20 samples are processed on an average per week in industrial sites where results are returned immediately rendering automation worthless.) Some lab testing instruments have been simplified but not enough to make them simple for the industrial operator. Testing instruments built exclusively for the industry that provides a simple and easy way to understand changes in oil (contaminants as well as its conditions) are not currently available and are very needed.

4. Current test methods measure strict parameters using standard and international units to satisfy lab standards and procedures. Lab analysis procedures follow standards set by associations such as the American Society for Testing and Measurement (ASTM) which are not required for determining machine condition. Some lab instruments provide parameters such as iron, lead, chromium, silver, boron, sodium, zinc, magnesium, titanium, molybdenum and antimony (components of oils additive packages and machine components) in parts per million (ppm). These parameters and units are meaningless to those operators and mechanics with little knowledge of chemistry in particular when industrial equipment is composed of mainly two elements (iron and brass). As a result they tend to file lab reports in a cabinet and do not use them to analyze machine problems as intended. A myriad of lab tests currently used to tests oils are based on many different parameters, many different indices which makes it hard to correlate results to understand the overall condition in a synergistic manner. Testing for oil and contaminants creates the need to know and understand a combination and a variety of units from different systems (English as well as Metrics, percentages, indices and parts per millions, etc.) which is confusing. The industrial operator is more concerned about knowing that there is a problem with the oil than knowing exactly how much ppm that is so important for the lab person. A test method with simple-to-understand parameters and units are not currently available and is needed.

5. Visual means are not currently being used for testing and analyzing critical and significant chemical and physical characteristics of oil. Only blotter tests are done visually. Industrial operator and maintenance personnel test and inspect products and machines using visual means on a daily basis. Oil analysis tests for blotter, color, opacity, and commonly found contaminants such as iron and brass, can be easily accomplished with visual means. Visual testing provides a universally accepted testing means that anyone can understand. Visual tests for properly testing and analyzing chemical and physical characteristics of industrial oils are not currently available and they are very needed.

6. A plurality of visual tests are not trended via software. Software for trending blotter test results, magnetic particles density distribution, solid contaminants removed on filters and magnetic means, color, opacity, and other testing means is not currently available. A software package that includes visual analysis for both chemical and physical characteristics of oil condition as well as particle analysis is not currently available. A software package that includes process parameters (temperature, speed, load, etc.) and helps understanding their effects is not currently available. A software package that contains information that is easily understood, simple and offers trended capabilities for oil characteristics and contaminants, is not currently available. A software package that satisfies all the previously mentioned characteristics is needed.

7. Chemical instability of a lubricant is the consequence of heat, mechanical stress and contamination. Oxidation of oil leads to changes in viscosity, increased acidity and the formation of degradation products such as gum, slime, varnish and sludge. Oil temperature and other process parameters such as vibration, speed, percent load, pressure and product significantly affect oil performance. Machines running at high speeds and high loads will produce more heat which will in turn cause the oil to breakdown faster than when running under no stress. These process parameters that change oil conditions are never entered nor considered in the oil analysis. Oil testing equipment and methods to include process parameters for testing and analysis is not available and is needed.

8. Test equipment currently available for testing oil contaminants has particle size limitations. Particle counters, can only test for particles of limited size range, current atomic emission spectrographs are most sensitive to particles having a size of approximately 10 microns or less. This problem eliminates or diminishes trending which is the most important and popular troubleshooting technique known in the industry. Test equipment for oil contaminants with no particle size limitations is not currently available and is needed.

9. Test equipment has been designed for lab environments and not for the industry. Test instruments for oil condition/contaminants aren't portable. Portability is critical for testing several machines on site, in particular when in remote sites. Portability is critical when testing machines with small amounts of oil that if a sample is taken, it may take all of the oil in the reservoir. Portable test equipment for oil analysis is needed.

10. Destructive testing techniques currently available remove all evidence of failure from oil samples. This eliminates the possibility of further analyzing or visually documentating the contaminant. Maintenance personnel/operators avoid further failure through looking at evidence of failure of product and machine components through a process called Failure Mode and Effect Analysis (FMEA). Test of destructive nature eliminate the capability of performing FMEA. Non-destructive test equipment for oil analysis is not currently available and is needed.

11. Current filter patches are hard to identify, handle, prepare and trend. They are easy to mislabel, easy to misplace and particles can be lost from filters if not properly handled. This makes filter patching a difficult task for the operator and maintenance mechanic who lacks delicate tools available in commercial labs. A holding means for filter patches is needed for Failure Mode and Effect Analysis (FMEA) purposes. Machine specific filter patch holders are not currently available and are needed.

12. Current blotter papers are hard to identify, handle, prepare and trend. They are easy to mislabel, ink tends to blur when writing on it, they are easy to misplace and blotter shape can be modified if not handled properly. This makes blotter paper making a difficult task for the operator and maintenance mechanic without the proper delicate tools available in any commercial labs. A holder for blotter is needed for FMEA purposes. Machine specific blotter holders are not currently available. A more practical means for holding blotter paper is needed. Machine specific blotter holders are not currently available and are needed.

13. A plurality of tests must be performed to every sample to fully assess the oil condition and contaminants as the following chart shows:

|  | Oil Degradation | Non Metals | Metals |
| --- | --- | --- | --- |
| *Spectrometric Analysis | X | X | X |
| Particle Counting | — | X | X |
| Direct Ferrography | — | — | X |
| Micropatch | — | X | X |
| Analytical Ferrography | — | X | X |
| Viscosity | X | — | — |
| Infrared Spectroscopy | X | X | — |
| Total Acid Number | X | — | — |
| Total Base Number | X | — | — |
| Fuel Contamination | — | X | — |
| Water Contamination | — | X | — |

*Spectrometric Analysis is performed in outside labs and is very limited by particle size.

Current tests do not test for all critical characteristics in a consistent, reliable and repeatable manner. A tester that provides in one single unit, the solution to oil characteristics and contaminants is not available and is needed.

14. The combination of tests currently available doesn't provide a synergistic and holistic solution for fluids and contaminants testing. Current testers of more than one oil characteristic tend to do that by simply adding testers in a piggyback manner. This tends to add results that are confusing and don't add to simplify a very complex procedure. There is no process or methodology to properly use these testers. A process and method that provides synergistic and holistic results for the industry is not available and is needed.

Objects and Advantages

Accordingly, several objects and advantages of my invention are:

a) To provide an instrument for separating contaminants prior to testing and analyzing oil characteristics b) To provide a process for separating of contaminants for properly testing and analyzing chemical and physical characteristics of oil and its contaminants c) To provide a testing instrument built exclusively for the industry that provides a simple and easy way to understand changes in oil (contaminants as well as its characteristics)

d) To provide test methods with simple parameters and units e) To provide an instrument, a method and software that uses visual means for properly testing and analyzing chemical and physical characteristics of oil and its contaminants f) To provide a software package that analyzes a plurality of oil characteristics, and does it using visual trending and visual analysis g) To provide an analytical instrument that includes process parameters h) To provide an instrument to test for oil contaminants with no particle size limitations i) To provide a portable test equipment for oil analysis j) To provide a non-destructive test method and equipment for oil analysis k) To provide a method specific filter patch holder l) To provide a method specific blotter holders m) To provide a tester contained in one single unit and provides a solution to oil characteristics and contaminants n) To provide a process, equipment and a method that provides synergistic and holistic results for testing oil in other than lab settings.

Further objects and advantages are to provide a easy to learn process for plant operators whose machines uses oil, a method for recycling oil after the separation of contaminants, to check for incoming quality of oil. Still further objects and advantages of my invention will become apparent from a consideration of the drawings and ensuing description.

DRAWING FIGURES

In the drawings, closely related figures have the same number but different alphabetic suffixes.

FIG. 1 shows a general block diagram illustrating the process of the invention FIG. 2 shows a perspective view of a typical embodiment of the entire system FIG. 3 shows a perspective view of the oil sample discharge apparatus FIG. 4A shows a magnetic particle separator apparatus FIG. 4B shows a density ruler pivoted to turn 360 degrees FIG. 5 shows a non-magnetic separator and a liquid separator apparatus FIG. 6 shows a filter and blotter assembly FIG. 7 shows a testing apparatus FIG. 8 shows data entering flow chart FIG. 9 shows physical and chemical analysis flow chart FIG. 10 shows contaminant analysis flow chart FIG. 11A shows trending of process and chemical parameter trends in a graphic and visual display FIG. 11B shows trending of oil characteristics (blotter image and opacity trends) in a graphic and visual display FIG. 12A shows oil application properties, parameters data entry and contaminants trending and visual display software FIG. 12B shows magnetic and non magnetic contaminants trending and visual display software

| List of Reference Numerals | | | |
|---|---|---|---|
| 13 | Discharging step | 82 | filter |
| 14 | Separating step | 84 | mesh |
| 15 | Preparing step | 86 | screen |
| 16 | Testing step | 87 | Adhesive band |
| 17 | Entering step | 88 | through-hole |
| 18 | analyzing step | 90 | vacuum funnel |
| 20 | housing | 92 | vacuum port |
| 22 | discharge apparatus | 94 | vacuum line |
| 24 | separation apparatus | 96 | vacuum valve |
| 26 | testing apparatus | 98 | clamp (pressure) |
| 28 | visual apparatus | 100 | flask |
| 29 | LCD/CRT display | 102 | flask connector |
| 30 | Operator interface of PC | 104 | heating device |
| 31 | Keyboard | 106 | condensing flask |
| 32 | vacuum source | 108 | springs |

-continued

| List of Reference Numerals | | | |
|---|---|---|---|
| 34 | vacuum line | 110 | condensate container |
| 36 | vacuum port | 112 | Ball drop type viscometer |
| 37 | air release cavity | 114 | Column |
| 38 | thermometer cavity | 116 | funnel |
| 40 | temperature measurement device | 118 | holder |
|  |  | 120 | ball |
| 42 | oil line port | 122 | valve |
| 44 | oil line | 124 | ball removal chamber |
| 46 | oil container lid | 126 | ball stop |
| 47 | Valve lid | 128 | upper fitting |
| 48 | oil container | 130 | top sensor |
| 50 | oil container handle or holder | 132 | lower sensor |
|  |  | 134 | magnetic plug |
| 52 | valve | 136 | lower fitting |
| 54 | valve opening | 138 | tester container |
| 56 | clamp | 140 | Blotter tester |
| 58 | particle density distribution ruler | 142 | Opacity tester |
|  |  | 144 | Color tester |
| 59 | numeral | 146 | Capacitance (electrical) tester |
| 60 | magnet | 148 | TAN tester |
| 62 | ruler guards | 150 | TBN tester |
| 64 | pouring lip | 152 | Blotter assembly |
| 66 | arms | 154 | Blotter paper |
| 68 | container | 156 | Base |
| 69 | pivot point | 158 | through-hole |
| 70 | angle | 160 | camera and lens |
| 71 | Backplate | 162 | microscope |
| 72 | drainage plug | 164 | stage |
| 74 | drainage line | 166 | visual base |
| 76 | drainage container |  |  |
| 78 | filter assembly |  |  |
| 80 | base |  |  |

SUMMARY

A process, a method and apparatus for testing oils that provides:

A process to separate contaminants for better testing of oil's chemical and physical characteristics and including manufacturing/operation parameters.

A method to simplify testing oils using visual, chemical and physical testing and analyzing results using software for trending.

An apparatus that has no particle size limitations, uses non-destructive testers, assembled in a single rugged and portable unit for industrial environments.

Description of Process—FIG. 1

FIG. 1 shows a process for separating, testing and analyzing a sample of used oil to properly test oil's physical and chemical characteristics, to properly identify contaminants and to assess severity of component's failure.

The initial step is that of discharging oil (13) to disperse contaminant particles reducing clumping. This is critical for producing a better particle density distribution. Discharging oil (13) is used to remove air bubbles which is critical for opacity test.

The second step is that of separating contaminants from oil (14). This step is accomplished prior to testing oil and contaminants (16). The contaminants are separated into magnetic, non-magnetic and liquids. Separating magnetic and non-magnetic provides a better differentiation between bearing failures (steel) and gears failure (bronze). Separating liquids such as water or glycol from oil provides for testing of intrinsic physical and chemical characteristics of oil.

The preparing separated oil and contaminants step (15) is accomplished after separating contaminants from oil (14). During step (15), oil testers are readied and oil is dispensed to them. Rinsing of magnetic and non magnetic contaminant particles is performed outside oil avoiding the introduction of solvents into the oil.

Testing oil and contaminants (16) step is accomplished with a plurality of testing procedures and techniques to provide easier to understand visual and trending information about oil condition and contaminants.

Entering data (17) such as manufacturer, vendor, storage location and container, physical and chemical characteristics is important for baseline forming and for analyzing contaminants origin. Entering data (17) about machine process provides clues about effects of process on oil condition. Entering data (17) from testing can be automated or manual.

Analyzing oil and contaminants (18) is accomplished using software for trending test results in a visual manner, correlating contaminant origin to oil condition or contaminants. Software analysis correlates machine process data to oil physical and chemical characteristics and contaminants. From the description above, a number of advantages of the oil and contaminant analyzer invention become evident:

a) it provides an instrument, a method and software that uses visual means for properly testing and analyzing chemical and physical characteristics of oil and its contaminants
 b) it provides test methods with simple parameters and units, non-destructive characteristics
 c) it provides an environment for separating and preparing oil and contaminants
 d) it provides a process for separating of contaminants for properly testing and analyzing chemical and physical characteristics of oil and its contaminants
 e) it provides a process, equipment and a method that provides synergistic and holistic results for testing oil in other than lab settings Description of Apparatus. FIGS. 2 to 7

A perspective view of a typical embodiment of the entire system of the present invention is illustrated in FIG. 2 which shows a housing (20), a discharge apparatus (22), a separation apparatus (24), a testing apparatus (26), a visual apparatus (28) and a operator interface or Personal Computer (30).

FIG. 3 shows a perspective view of the oil sample Discharge Apparatus (22) comprising: An oil container (48) is supported to the housing (20) by a u-shape clamp (56). However a cavity from 10 mm to 15 cm on the housing can be used to support container (48). Container (48) is preferably made out of clear glass, however other material that can sustain high temperatures such as Teflon, acrylic, aluminum, steel, etc. can be used. Container volume is from 50 ml to 1 L. Said container has a handle (50) used to keep operator's hands away from the hot oil being extracted from the machine's reservoir. In another embodiment, the volume is from 1 L to 1,000 L. An oil container lid (46) that screws in the oil container (48) comprises of a vacuum port (36) connected through a vacuum line (34) and through a vacuum valve (96) to a vacuum source (32) available commercially to draw vacuum when the oil container (48) is closed. Vacuum source can be powered by available sources such as air, electricity or manually.

An oil line port (42) is connected to an oil line (44) that provides a path for the oil to flow from the machine's reservoir to oil container (48) conveyed by vacuum source (32). Oil line (44) is supported by modular hose manufactured by Loc-Line for rigidity and directionally. In another embodiment, the oil line port (42) is used to release trapped air after oil is drained. A thermometer cavity (38) is used for inserting a temperature measurement device (40) such as a thermocouple based digital thermometer and is used to measure fluid's temperature as it is extracted from machine's reservoir. Another embodiment uses a mercury-filled thermometer for temperature measurement device (40) with an o-ring to mark on temperature.

A valve (52) is connected to a valve lid (47) that screws on the oil container (48) and is available commercially. Valve opening (54) is from 1 mm to 10 mm width to provide a stream of oil flow between 0.5 mm to 10 mm wide and therefore dispersing particles more evenly over the particle's density distribution ruler (58). In another embodiment, the valve opening (54) can rotate from 181 degree to 359 degree with the horizontal line and along the magnet (60) length to dispense oil at varied distances on the particle density distribution ruler (58). In another embodiment, valve lid (47) is at one end of the container while oil container lid (46) is at the other end of same container (48). In another embodiment, valve (47), container lid (46) and container (48) are all built in one single unit.

FIG. 4 shows a perspective view of a magnetic separator apparatus (23) comprises of a particle's density distribution ruler (58) placed below valve opening (54) and over the magnet (60). Said ruler is graded with numerals (59) to provide an indication of the magnetic particle size. A low numeral will correspond to smaller particles as they are attracted by magnetic force at the lower end of ruler. A high numeral will correspond to larger particles as they are attracted by magnetic force at the higher end of ruler (58). Said numerals are placed along the longest side of said ruler and parallel to the length of the magnetic field force. In another embodiment, the numerals are made with letters such as a, b, c, etc, colors such as green for smaller particles, yellow for medium particles and red for larger particles or other graphics representing particles of lower to higher sizes. In the preferred embodiment, ruler is of thin temperature resistant plastic material of rectangular shape from 0.5"×4" to 3"×10", however it can be made of glass, paper, aluminum, etc. Ruler is preferably white to enhance the background between the particles and the background. However other colors such as silver, black, red, etc. can be used to enhance process particles of contrasting colors. Process information such as machine number, work order number, technician who performed the task can be written on ruler (58). Said ruler is removable and fits within ruler guards (62) which are used to restrict lateral oil flow. Ruler terminates in a triangular shaped pouring lip (64) and is sloped vertically downwards by two arms (66) to direct fluid flow towards container (68). A magnet (60) is placed under the particle's density distribution ruler (58) to attract magnetic and magnetized particles suspended on oil flowing over ruler (58). In the preferred embodiment, this magnet is a permanent magnet sintered or cast, made of materials such as alnico, ceramic, or rare earth, available from manufacturer Bunting Magnetics. The preferred embodiment is rare earth material of rectangular shape from 0.5"×4" to 3"×10", width from 0.25" to 2". However other sizes and shapes can be used. Said magnetic means can be of variable type powered by an alternating current source.

Magnet (60) is inclined and pivoted (69) to use gravitational forces to aid oil flow by forming an angle (70) with the horizontal varying from 179 degrees to 91 degrees as shown in FIG. 4-B. A back plate (71) is used to increase magnet strength and directionality and is made out of metal as shown in FIG. 4-A. A ruler guard (62) is placed at both sides of magnet (60) and along fluid flow to keep flow aligned with magnetic force field and to protect magnet (60) from being damaged. In another embodiment, the magnet and the particle density distribution ruler (58) is illuminated with visible light means such as white or ultraviolet fluorescent or incandescent light and positioned adjacent to said magnet for easier visual inspection of particles on site. In another embodiment, a lens of predetermined magnification power is mounted directly above the magnet to allow operator's visual inspection.

FIG. 5 shows a non-magnetic separator (25) comprising of a container (68) of cylindrical or rectangular shape, from 1 to 20 centimeters long and 0.5 cm to 15 cm radius, made of plastic, metal or glass. Said container (68) comprises of a drain plug (72) at the bottom of container (68), used for drainage of oil in the event of filter assembly (78) becomes plugged up. Drain plug is connected to drainage line (74) to direct fluid to drainage container (76). Another embodiment allows drain plug (72) to drain oil to a drainage container (76). Another embodiment allows a by-pass filtration system where filters of larger porosity are used to continue the filtration process and then connect to vacuum funnel (90). A filter assembly (78) is shown in FIG. 6-a and comprising of a base (80), a filter (82), a mesh (84), and another base (80) sandwiching filter (82) and mesh (84). A screen (86) supported by vacuum funnel (90) provides support to mesh (84) and filter (82) under vacuum pull. Assembly (78) comprises of a base (80) made of paper or plastic paper or plastic or adhesive tape from 0.2 mm to 4 mm in thickness and has an overall dimensions roughly from 2 cm×4 cm (rectangular shape) to 7 cm×20 cm. Base (80) is of a surface that can be written or imprinted on. Operator taking oil sample writes on base (80) data pertinent to machine number, date, work order number, technician names and a section to allow for operator's comments. After taking the sample, operator encloses the filter assembly by peeling of the adhesive (87) and placing a see-through cover sheet on top of it to seal particles in assembly, to keep assembly cleaner and to allow for visual inspection. At one end of the base (80) is a through-hole (88) that has an overall dimensions from 0.25 cm to 9.5 cm in diameter. Through-hole (88) could take the shape of a square or rectangle and is concentric to filter (82), mesh (84) and screen (86). Filter (82) is a membrane of predetermined pore sizes and types. The preferred embodiment uses a polycarbonate membrane filter however other types such as nylon, fiber or paper can be used. Different colors may be used for contrasting different contaminants. Filter (82) and mesh (84) are adhered directly to the base (80) by means of heat or adhesive. Base (80) is adhered on to another base (80) sandwiching its entirety and allowing fluid to pass through a through-hole (88). A plurality of filter assemblies (78) can be used in parallel allowing for different pore sizes to be used simultaneously. Assembly (78) is used between a container (68) and a vacuum funnel (90) by means of a clamp (96) to pressurize vacuum funnel (90) to minimize leakage. Clamps (56) can be made of rubber, metal or other materials and are available commercially. Vacuum funnel (90) contains a vacuum port (92) connected to a vacuum line (94). Said vacuum line (94) is connected to vacuum source (32). A valve (96) directs vacuum source (32) to vacuum line (94) and to vacuum line (34). Vacuum funnel (90) is made of glass in the preferred embodiment, however plastic or metals can be used according to the fluid compatibility.

A liquid separator shown in FIG. 5 comprising of a flask connector (102) that connects funnel (90) to the flask container (100). Flask container (100) is made out of glass connected to a vacuum funnel (90) and is supported by a heating means surface (104). Other components such as iron or aluminum can be used for the flask container (100). A condensing flask (106) is used to guide condensation towards the condensate container (110) and is available commercially. Container (110) has lines to visually indicate liquid condensate volume. Condensing flask (106) can use cooling means to reduce condensing times a compressing means such as springs (108) are used to hold the condensing flask (106) and condensate flask (110) tight to avoid vapor and fluid leakage. A heater (104) is used under a flask (100) to provide the heating energy needed to separate the different liquids from the oil after reaching liquid's boiling point. In another embodiment, other physical means such as allowing the denser fluid to settle down with time can be used. In another embodiment, chemical means such as the addition of special additives used to separate fluid from liquid can be used. In another embodiment, oil is separated by placing a drop directly over the heater (104).

FIG. 7 shows a perspective view of the Fluid Preparation Apparatus (26) comprising of a ball drop type viscometer (112) which comprises of a hollow cylindrical column (114) of length from 5 cm to 30 cm. The diameter of the column is from 0.5 cm to 5 cm. Said column can be coated with epoxy and plastic shielded for protection. The column contains commercially available components such as: funnel (116), holder (118), ball (120), valve (122), a ball removal chamber (124), a ball stop (126), fittings (128 and 136) and a magnetic plug (134). Funnel (116) is secured to the higher end of column (114) by means of said fitting (128) to collect and direct oil and ball (120) into the column's interior. A ball stop (126) directs a ball (120) to the ball removal chamber (124) and is about 0.5 cm to 4 cm under lower sensor (132). The ball stop (126) allows fluid to pass around the ball into a valve (122) and impedes ball from plugging valve (122). Ball (120) is retained at the ball removal chamber (124) by means of a magnetic plug (134). A valve (122) is secured by a fitting (136) to the lower end of a column (114). A support means (118) is used to hold a column (114) to the housing (20). Holding means is of a jaw type to allow for column removal and relocation and is available commercially. Jaw type clamp is opened to allow for removal of column (114) to dispose of remaining fluid after fluid has been delivered to tester container. Top sensor (130) is placed at a predetermined distance from upper fitting (128). Top sensor (130) provides a signal to a CPU that starts an internal timer as programmed by software. Lower sensor (132) is placed at predetermine distance from lower fitting (136) and provides a signal to a CPU that stops the timer started by Top sensor (130). A ball (120) is used to activate said top sensor (130) and lower sensor (132) and is from 0.5 cm to 3 cm in diameter. The gap between ball (120) and the column (114) I.D. is from 0.5 mm to 5 mm. The preferred embodiment uses a steel ball, however other material such as glass or tantalum can be used for testing different types of viscous fluids. This will require using pressure means such as springs to replace magnetic plug (134). Valve (122) is placed above tester container (138) and is used to dispense oil to said tester container. Said valve is from 0.5 cm to 5 cm from container to allow enough space for different testers.

FIG. 7 shows a tester container (138) placed under valve (122) and used to contain chemical and physical type testers. Tester container (138) comprises a plurality of cavities used for placing a plurality of tester such as blotter tester (140), opacity tester (142), color tester (144), capacitance tester (146), total acid number tester (148) and total base number (150) tester. The tester container is from 3"×8" to 5" to 10" rectangle and height is from 1 cm to 10 cm. In another embodiment, said container is of circular shape of radius from 5 cm to 30 cm to rotate the plurality of testers under valve (122). In another embodiment, said container is automated to rotate or slide the plurality of testers under valve (122) or moving a column (114) to over each tester.

A blotter tester (140) is used to test dispersion of oil on absorptive medium comprising of a blotter paper (154) available commercially placed under valve (122) and on the tester container (138) to dry out. A predetermined amount of oil is drained from a valve (122) into a blotter tester (140). Another embodiment supports the blotter tester (140) in a blotter assembly (154) is shown in FIG. 6-B Blotter assembly (154) comprises of a paper or plastic base from 0.2 mm to 4 mm in thickness and has an overall dimensions from 2 cm×4 cm of rectangular shape to 7 cm×20 cm. The paper or plastic base (156) is of a surface that can be written on. Information to write on blotter frame comprises data pertinent to machine number, date, work order number, technician names and a section to allow for comments. After taking the sample, operator encloses the blotter assembly by peeling of the adhesive (87) and placing a see-through cover sheet on top of it to allow for visual inspection. At one end of the blotter assembly (152) is a through-hole (158) that has an overall dimensions from 0.25 cm to 9.5 cm in diameter. Through-hole (158) is concentric to the blotter paper (154). Blotter paper is chromatography paper available commercially. Said blotter paper (154) is from 1 cm to 5 cm in diameter or of rectangular shape from 1 cm to 6 cm sides. A blotter paper (154) is attached by adhesive means to the back of said paper or plastic base (156) and overlapping a through-hole (158) to seal tight and allow no fluid to leak through.

An Opacity tester (142) is used to test for changes in the opacity of oil. Opacity tester (142) is placed under valve (122) for collecting a predetermined amount of fluid and on the tester container (138). An opacity tester (142) comprises of a light source and a light detecting means such as a phototransistor that produces a signal (voltage or current) proportional to the change in opacity of the oil. Another embodiment allows for opacity tester (142) to be placed next to top sensor (130) for opacity testing.

A color tester (144) is used to test for oil and liquid contaminant color and comprises of a see-through sieve placed under valve (122) and on a tester container (138). However another color of sieves such as white can be used for contrasting colors. Other fluids can be contained by said sieve. A predetermined amount of fluid is drained from a valve (122) into a sieve. Said sieve is removed from tester container (138) and be placed under visual means for documenting results.

A Capacitance tester (146) is used to test for oil's dielectric capacitance and comprises of a capacitor sensor placed under a valve (122) and in a tester container (138) where a predetermined amount of fluid is released into the capacitance tester (146). Said capacitor provides a signal proportional to the dielectric capacity of fluid being tested and it is commercially available.

A Total Acid Number, abbreviated as TAN, tester (148) is used to test for acidity changes in oil and comprises of a TAN tester placed under a valve (122) and in a tester container (138) where a predetermined amount of fluid is released. Said tester is available commercially and manufactured by Dextril.

A Total Base Number, abbreviated as TBN, tester (150) is used for testing acidity changes in oil and comprises of a TBN tester (150) placed under a valve (122) and in a tester container (138) where a predetermined amount of fluid is released. Said tester is available commercially and manufactured by Dextril. Although the tests and testers described above contain many specificities, these should not be construed as limiting the scope of the invention but as merely providing illustrations of some of the presently preferred embodiments of this invention.

FIG. 2 shows a perspective view of the Visual Apparatus (28) comprising of stage (164) where human vision enhanced by lenses is used to inspect results of oil and contaminant tests. Information can be compared with existing documentation or reports previously filed. Mechanical and digital means to record visual information such as cameras, video recorders, etc. are used to record and document said oil condition tests results and said separation process results. The preferred embodiment is to use a digital camera (160) with a variety of lenses supported by a stage (164). A light source is placed under the stage. All visual means are available commercially. Another embodiment uses a mechanical means such as a Polaroid or a 35 mm camera which does not require electrical connections and can be used in remote sites.

A means to view small particles such as a microscope (162), is used for inspecting particles removed during magnetic and non-magnetic separation. A light source placed on top of a microscope eyepiece is used for illuminating particles under the microscope. This light is coaxial to lenses and is available commercially.

A camera-scope adapter is needed to connect camera to microscope. A C-type fitting connects camera to microscope eyepiece. Electrical and optical adapters, connectors and lenses are added or interchange for communications to CPU and to obtain greater optical magnification. A visual base (166) is used to place articles to be documented visually.

FIG. 2 shows a perspective view of the a operator interface or Personal Computer apparatus (30) comprising an LCD or CRT (29) screen used to display information and to prompt action. A PC or user interface keyboard (31) is used to manually enter process and testing results data. Said keyboard is connected to user interface of CPU via communication cables. In another embodiment, data entry can be done automatically via cabling and connections to a plurality of sensors and testers. In the preferred embodiment, the PC or user interface is positioned internally, however it can be placed totally or partially externally to housing (20). Interface cabling is used for communicating sensors to internal logic, camera to CPU, peripherals, etc. Electronic signal conditioning means may be added to PC for providing the proper voltages and current levels from inputs/outputs to CPU of the user interface or PC. Visual Basic software programming is used for the software algorithms, however other software languages can be used. Software program is loaded into user interface CPU or PC to carry on process algorithms, print results and reports. Digital camera software is integrated to process. Images from digital camera are sent to the process software via cabling means. Components are available commercially. Preferred embodiment uses a commercially available Pixera camera and software.

In another embodiment the apparatus is fully automated. Fluid separator is connected to viscosity column and tester container rotates automatically to receive predetermined quantities of oil and to document results.

In another embodiment, the apparatus comprises of a vibration tester, ultrasonic tester, temperature tester, process parameter testers all combined to provide a synergistic result about machine performance.

In another embodiment, the process is applied to large amounts of oil requiring larger sizes and types of magnets, larger containers and larger flowing mechanisms.

From the description above, a number of advantages of the oil and contaminant analyzer invention become evident:

a) it provides an instrument for separating contaminants prior to testing and analyzing oil characteristics
b) it provides a testing instrument built exclusively for the industry that provides a simple and easy way to understand changes in oil (contaminants as well as its characteristics)
c) it provides an instrument to test for oil contaminants with no particle size limitations
d) it provides a tester contained in one single unit that is portable
e) it provides an instrument, a method and software that uses visual means for properly testing and analyzing chemical and physical characteristics of oil and its contaminants
f) it provides a filter patch and blotter holders
g) it provides a process, equipment and a method that gives a synergistic and holistic results for testing oil in other than lab settings.

Description of Method. FIGS. 1 to 6, 8, 9, 10

FIG. 3 shows how an oil sample is suctioned from a machine's oil reservoir using an oil line (44) and discharged into the oil container (48) where the temperature is measured and recorded. Opening valve (52) releases a controlled stream of oil from container (48). Controlling the width and amount of oil will reduce particle clumping and improve particle dispersion. Gravity forces the fluid downwards dissipating air bubbles due to friction between the oil and the particle density distribution ruler (58).

FIG. 4 shows oil flowing over the particle density distribution ruler (58) where a magnet (60) is attracting and removing all magnetic and magnetized particles from oil flow and depositing particles on top of the ruler (58) and along the magnetic field according to their size and volume. Oil flows downwards and over the pouring lip (64) into container (68).

Figure 1:
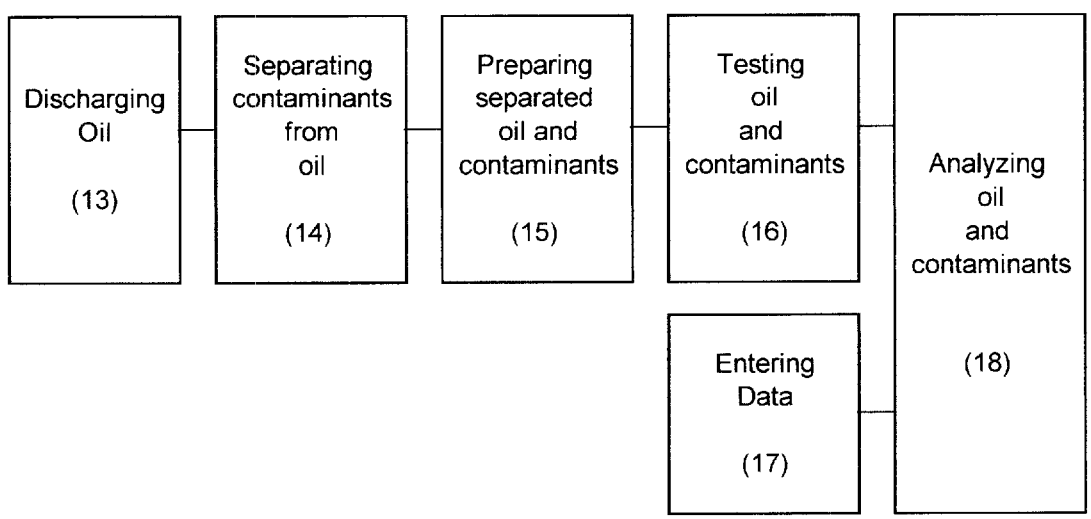

FIG. 1 shows the preparing separated oil and contaminants step (15) that comprises of several actions such as: removing and relocating particle density distribution ruler (58), rinsing with an oil cleaner and avoiding in this manner fluid contamination. Removing and relocating filter assembly (78) from clamp pressure, rinsing with oil cleaner and avoiding fluid contamination. Emptying condensate container into color tester (144). Emptying flask (100) into column (114). Releasing ball (120) into column (114). Removing ball (120) from ball removal chamber (124). Preparing TAN (148) and TBN (150) testers (with predetermined solvents, reagents, etc. Releasing a predetermined quantity of oil into TAN and TBN tester (148). Positioning blotter paper or blotter assembly (152) over blotter tester (140). Releasing a predetermine quantity of oil into blotter tester (140). Releasing a predetermine quantity of oil into color tester (144). Releasing a predetermine quantity of oil into capacitance tester (146). Preparing other testers as they are incorporated into the tester container (138).

Figure 2:
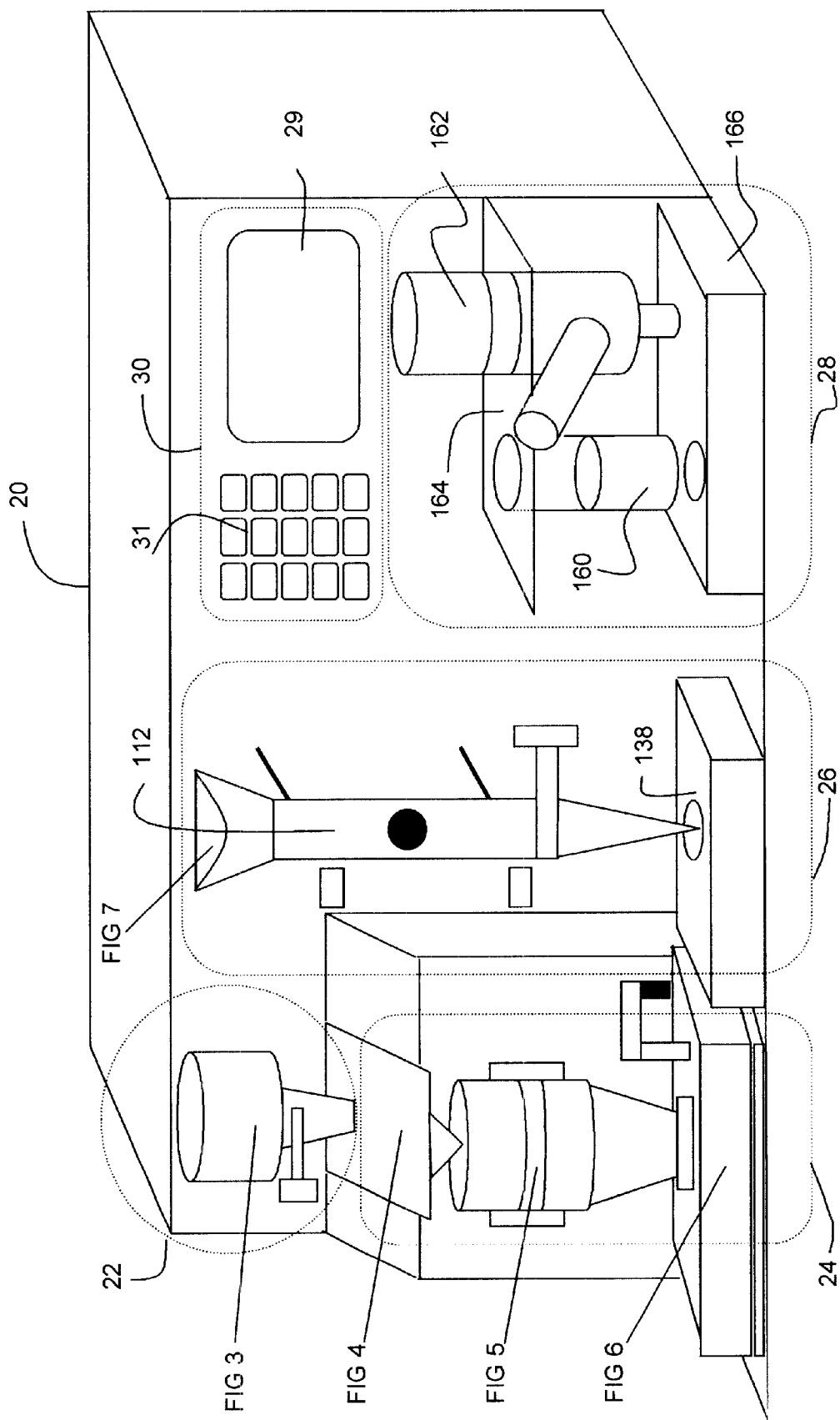
Figure 3:
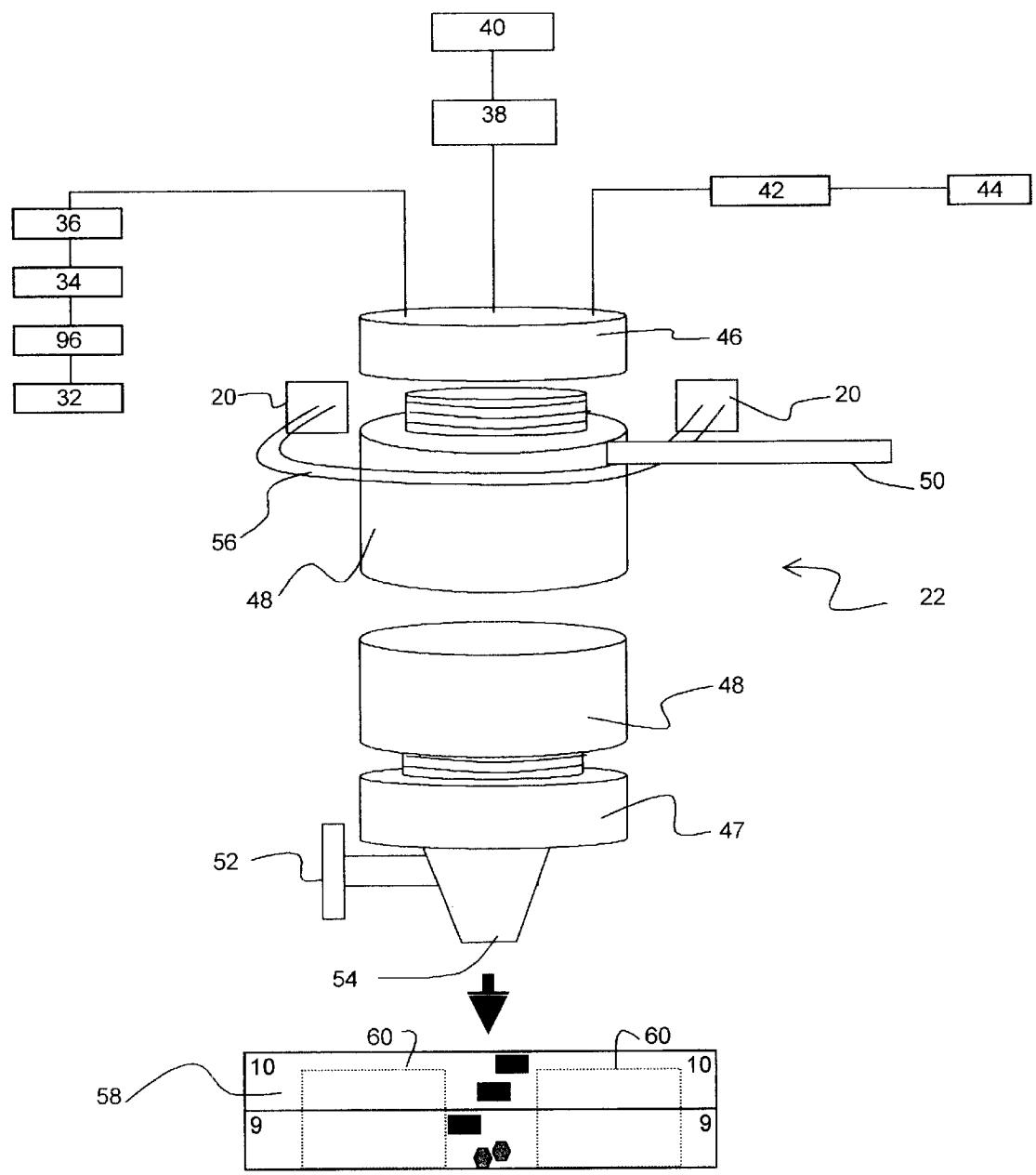
Figure 5:
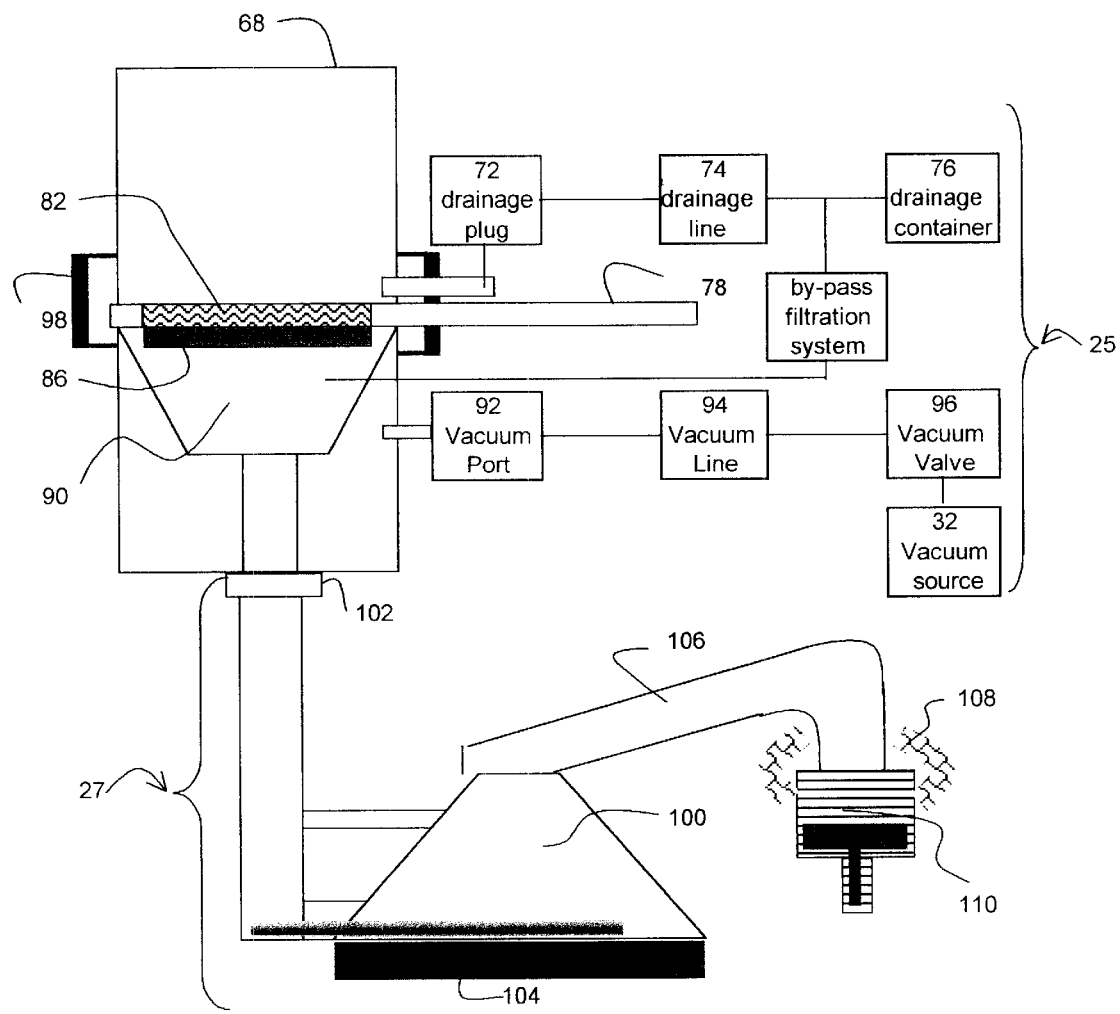
FIG. 5 shows the filter assembly (78) filtrating non-magnetic particles suctioned by vacuum source (32) and trapped by filter (82). After filtering the particles, oil continues flowing downwards through the funnel (90) and into the flask (100) where oil is heated condensating all liquid contaminants into container (110).
Figure 7:
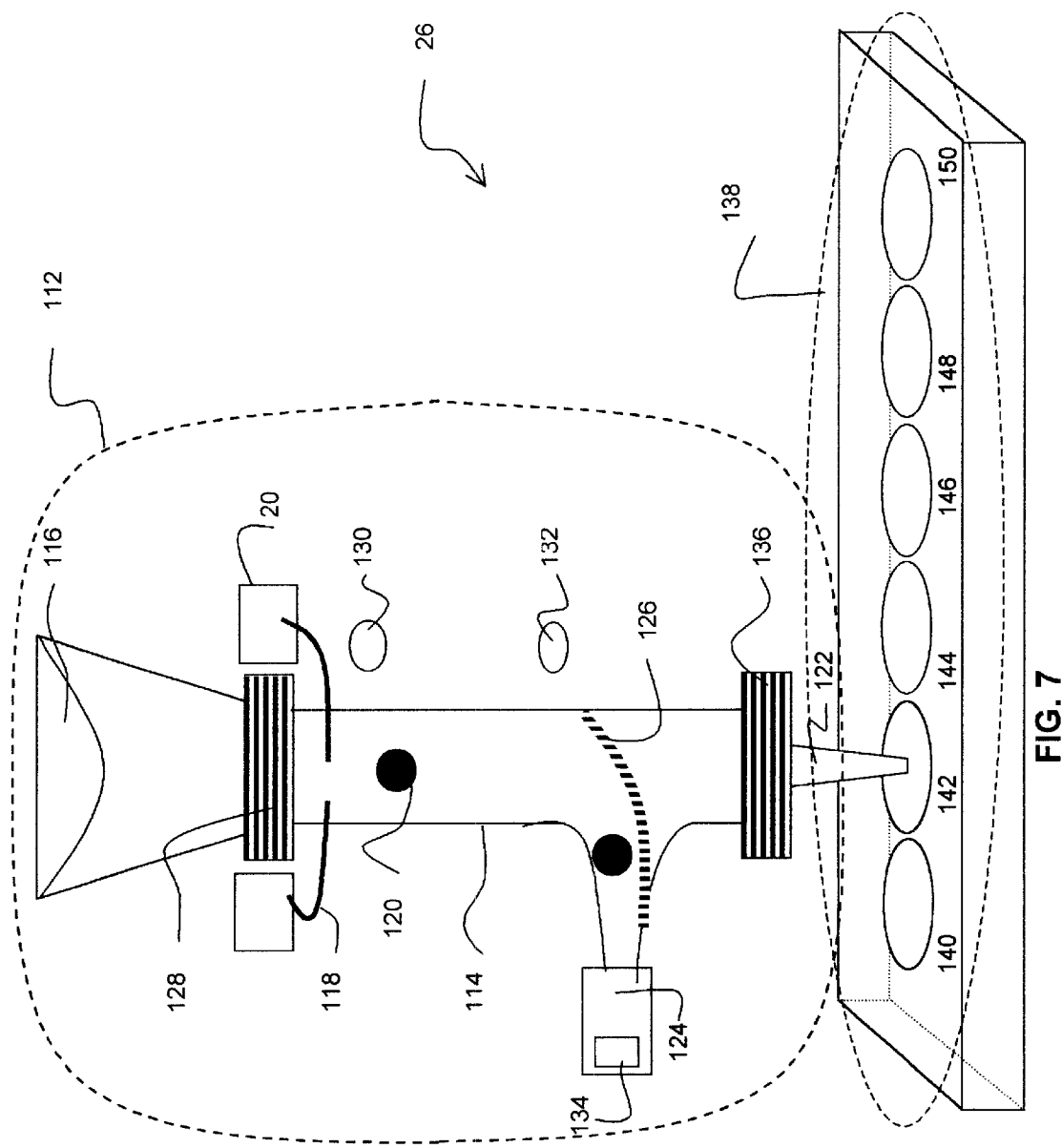

FIG. 2 shows tester container (138) used for testing oil. Testing oils comprises of testing several physical and chemical characteristics of oil such as viscosity using human vision and a timer. Another way of testing viscosity is by automatically measuring the time elapsed when ball falls in ball drop type viscometer tester (112). Another test to measure oil's chemical and physical characteristic is done by comparing blotter paper in tester container (138) with other previous tests, using industrial standards records for comparison and using a plurality of visual documenting means such as digital cameras (160). Testing TAN and TBN in tester container (138) using human vision to determine levels when using manual testing techniques such as Dextril's and using a plurality of visual documenting means such as digital cameras (160).

Testing color of oil using human vision, comparing with previous samples taken and using a plurality of visual documenting means such as digital cameras (160).

Testing liquid contaminants using human vision, comparing with previous samples taken and using a plurality of visual documenting means such as digital cameras (160).

FIG. 6 shows a graduated condensate container (110) from which volume reading directly can be obtained. In another embodiment, testing liquid contaminants is done using a drop of oil deposited over a heating device (104) and using a recording means such as microphone or ultrasonic sensor to determine the quantity of liquid contaminant. The voltage signal is proportional to the noise levels of water popping under the heating device. Such electrical output can be trended when input into the software process for analysis. Popping sound can be listened to by listening human.

FIG. 2 shows tester container (138) with opacity tester of fluid contaminants using human vision, comparing with previous samples taken and using a plurality of visual documenting means such as digital cameras (160). Testing oil's dielectric capacitance by using a capacitor's output in tester container (138) provides us with more information about testing oil's physical and chemical characteristics.

FIG. 2 shows the visual apparatus used for testing contaminants including a plurality of tests comprising of testing magnetic particle density distribution ruler (58) human vision to interpret location of particles in reference to numerals (59). Another method can be done by using a plurality of visual documenting means such as digital cameras (160) supported by stage (164). Testing magnetic particle types and sizes found in particle density ruler (58) using can be done by using human vision aided by low power (4×, 10×, etc.). Another way for testing is by using magnifying means such as lenses, a high power (40×, 100×, etc.) optical magnifying means such as microscope (162) to measure particle sizes, to identify color and shape of particles at the micron level. Using a plurality of visual documenting means such as digital cameras (160) is another testing technique. Testing non-magnetic particles using filter assembly (78) can be done with human vision and with a plurality of visual documenting means such as digital cameras (160). Testing non-magnetic particle types and sizes using filter assembly (78) can be done using human vision aided by low power (4×, 10×, etc.) magnifying means such as lenses. A high power (40×, 100×, etc.) optical magnifying means such as microscope (162) can be used to measure particle sizes, to identify color and shape of particles at the micron level and using a plurality of visual documenting means such as digital cameras (160).

Although the tests and testers described above contain many specificities, these should not be construed as limiting the scope of the invention but as merely providing illustrations of some of the presently preferred embodiments of this invention.

Figure 8:
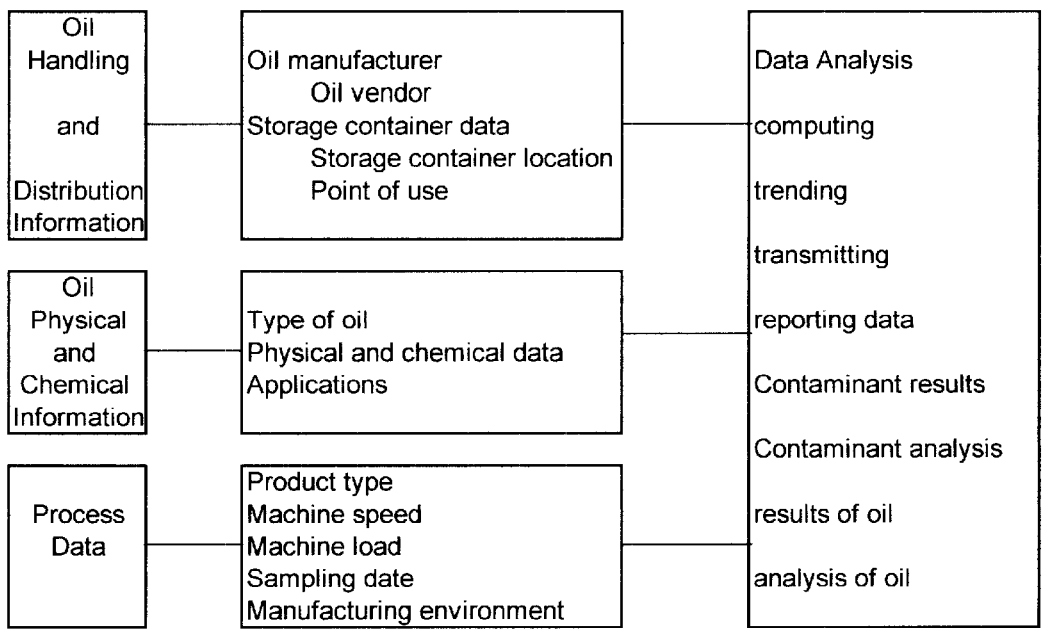

FIG. 8 shows the analysis that can be done with data entry of oil handling and distribution information. Managing lubricants before they reach their final destination and point of use requires providing information about oil manufacturer, vendor, storage containers, location of the oil reservoirs and oil storage means, quality control test results, safety and environmental regulations for oil. This part of the software routine is typically set up during the initial process establishment and may require little changes once completed. It is used to determine the origin of possible contaminants found in oil exposed to contaminants found in different areas such as storage, production, or machinery nearby. It is also used to compare data entered with database in case errors were made during the handling or storage.

Analysis can be done using information about type of oil, physical and chemical information obtained from manufacturer and entered as a baseline. This baseline can then be used for comparing to actual conditions and to check for quality problems or poor maintenance practices.

Analysis can be accomplished by using process and production information that affects directly or indirectly oil test results. Data such as product manufactured, machine speed and load, oil running temperature, date of sampling and other manufacturing characteristics affect oil condition and the software allows you to correlate the relationship among them.

Figure 9:
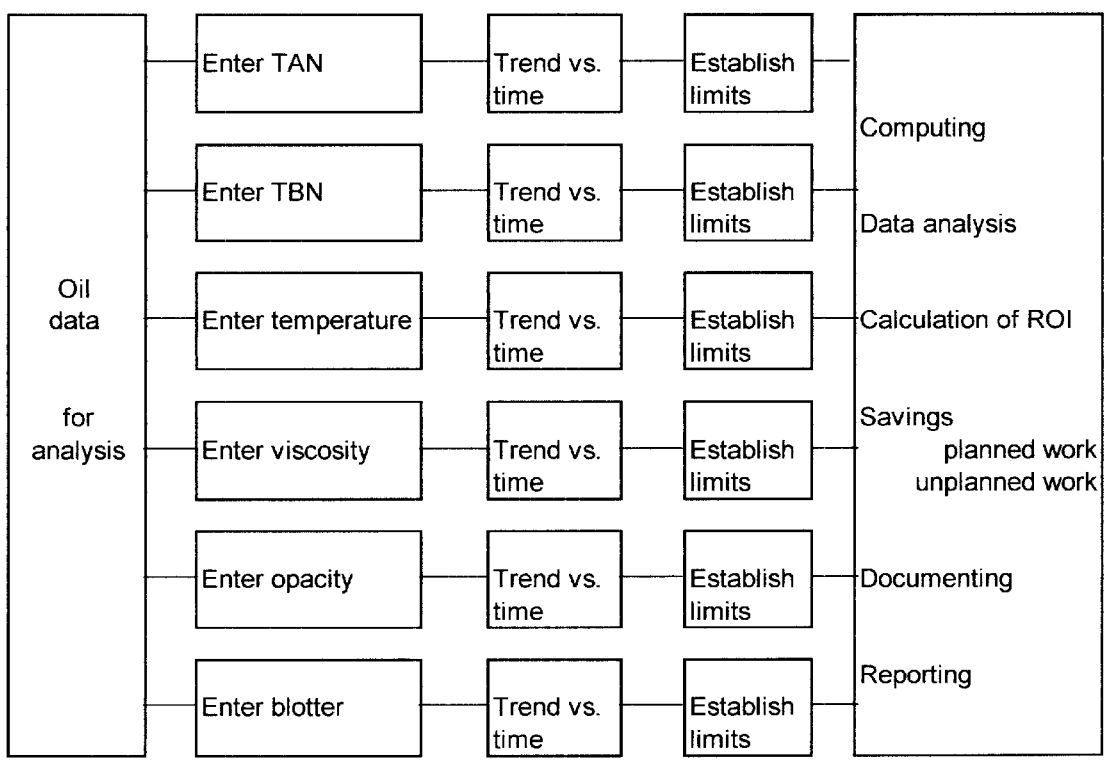

FIG. 9 shows the oil trending and analyzing using software comprising of trending and analyzing using software for oil temperature, process parameters such as rpm and percent, load and percent. Trending and analyzing viscosity using software. Trending and analyzing blotter paper using recorded visual images and software process for analyzing boundaries, spot size and dispersion of the oil on blotter paper. Trending and analyzing TAN/TBN using recorded visual images and software process. Trending and analyzing color of oil using recorded visual images and software process. Trending and analyzing liquid contaminants using recorded visual images and software. Trending volume reading directly from graduated condensating container (110). Trending and analyzing liquid contaminants can be done when the electrical signal from a microphone or ultrasonic sensor proportional to the heated liquid noise is quantified or display on CRT/LCD (29) display. Trending and analyzing opacity of fluids using visual images and software process. Trending and analyzing capacitance results using a software process.

Figure 10:
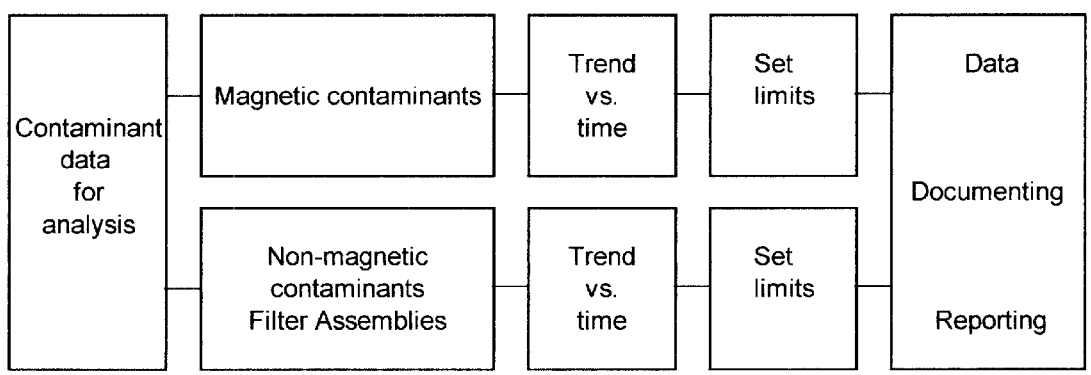

FIG. 10 shows analyzing contaminants data comprising trending and analyzing recorded visual images of magnetic particle density distribution ruler (58) using a software process. Trending and analyzing magnetic particle using microscopic images and software to measure particle sizes, to identify color and shape of particles at the micron level. Trending and analyzing recorded visual images of non-magnetic particles and using a software process. Trending and analyzing non-magnetic particle using microscopic images and software to measure particle sizes, to identify color and shape of particles at the micron level.

Software process is also used to calculate viscosity for the Ball drop type viscometer (112) which is done by acquiring and processing the signals from the two sensors (130 & 132). The time delay between sensors determines the time that the ball took to travel that distance. The viscosity is calculated by the formula: $\mu = K(\rho balls - \rho)t$, where $\mu$ is viscosity in centipoises (cp), ρballs is the density of ball, ρ is the density of fluid tested, t is the time of descent, K is the viscometer constant calculated with water-glycerol. In another embodiment of this patent, the time elapsed between the sensors is trended versus time to provide a time as a unit proportional to the viscosity of the fluid tested.

Process' return on investment is calculated to show the benefits of testing oils. Savings are calculated based on planned repair work versus unplanned repair work. Catastrophic failure cost is compared with minor repair cost that typically results when problems are detected early during the onset of failure.

Software documents and allows for trending, graphics, alarm setting, etc. Parameters are trended and documented using images or charts to show visually and graphically any significant differences. A baseline is determined and alarms set to indicate when a parameter is exceeding tolerance levels. Comparative analysis with previous existing data and baseline is done visually by observing person. Trend can be visual as well as numerical. The software provides correlation between process data and particles, such as non magnetic particles triggering questions about the origins of the particles. The software provides correlation between storage data and non-magnetic particles triggering questions about the origins of the particles. The software provides correlation between oil quality data and viscosity triggering questions about the possibility of having a different type of oil with a different type of viscosity. This can be triggered when there is a substantial difference between viscosity readings taken at close intervals.

Although the methods described above contain many specificities, these should not be construed as limiting the scope of the invention but as merely providing illustrations of some of the presently preferred embodiments of this invention. From the description above, a number of advantages of the oil and contaminant analyzer invention become evident:

a) it provides an analytical instrument that includes process parameters b) it provides a software package that analyzes a plurality of oil characteristics, and does it using visual trending and visual analysis c) it provides an instrument, a method and software that uses visual means for properly testing and analyzing chemical and physical characteristics of oil and its contaminants d) it provides test methods with simple parameters and units e) it provides a method specific filter patch and blotter holder

SUMMARY, RAMIFICATIONS AND SCOPE OF INVENTION

Accordingly, the reader will see that the oil and contaminants analyzer of this invention can be used to perform a plurality of tests and analysis, in a single and self-contained unit. This invention introduces a visual process that can be easily understood and implemented by the industrial operator and maintenance personnel who is used to test and troubleshoot process and machine problems using visual techniques. It also provides them with tools to show evidence of the contaminants found in the filtering assembly as well as deteriorating oil conditions as found on the blotter assembly. The oil and contaminant analyzer gives the industrial operator a process, an instrument and a method that will allow him or her to determine the condition of oil as well as the performance of the machine. The oil and contaminant analyzer provides a process, equipment and a method that gives synergistic and holistic results for testing oil in harsh industrial settings.

Thus the scope of the invention should be determined by the appended claims and their legal equivalents, rather than by the examples given.

The embodiment of the invention in which an exclusive property or privilege is claimed are defined as follows:

1. A process for separating, removing contaminants from, testing and analyzing a sample of oil comprising:
   a) Discharging oil and contaminants;
   b) Separating contaminants from said oil prior to removal;
   c) Removing non magnetic, magnetic and fluid contaminants from said oil;
   d) Preparing separated oil and contaminants after removing contaminants;
   e) Testing separated oil and removed contaminants;
   f) Analyzing the results of the tests of the separated oil and removed contaminants.

2. A process as recited in claim 1, wherein discharging oil contaminants comprise:
   a) Dispersing contaminants;
   b) Removing air bubbles and gases.

3. A process as recited in claim 1, wherein said separating contaminants comprise:
   a) Separating non magnetic contaminants;
   b) Separating magnetic and magnetized contaminants;
   c) Separating liquid contaminants.

4. A process as recited in claim 1, wherein said removing contaminants comprise:
   a) Removing non magnetic contaminants;
   b) Removing magnetic and magnetized contaminants;
   c) Removing liquid contaminants.

5. A process as recited in claim 1, wherein said preparing separated oil and contaminants comprise:
   a) Preparing oil testers;
   b) Dispensing separated oil;
   c) Rinsing contaminants after removing contaminants from said oil.

6. A process as recited in claim 1, wherein testing separated oil and removed contaminants comprise:
   a) Using a plurality of procedures and techniques for testing removed contaminants;
   b) Using a plurality of procedures and techniques for testing separated oil.

7. A process as recited in claim 1, wherein said analyzing the results of the tests of the separated oil and removed contaminants comprise:
   a) Using a microprocessor under control of software;
   b) Using oil physical and chemical data for building a baseline;
   c) Using oil manufacturer, oil handling and distribution data for analysis;
   d) Using machine and process information analysis;
   e) Correlating machine and oil parameters;
   f) Computing, transmitting, performing trending analysis and reporting results of oil and contaminants and process.

8. A process as recited in claim 7, wherein said performing trending analysis and reporting results of oil and contaminants comprise:
   a) Using imaging recording means and testing parameters for performing trending analysis of contaminants;
   b) Using imaging recording means and testing parameters for performing trending analysis of oil properties.

9. A apparatus for separating, testing and analyzing a sample of oil comprising:
   a) A discharge apparatus which discharges a oil sample into a separation and removal device;
   b) A separation and removal apparatus placed under the discharge apparatus to separate and remove magnetic, non-magnetic and fluid contaminants from oil;
   c) A testing apparatus which tests and analyzes magnetic and non-magnetic contaminants and chemical and physical properties of the oil sample free of solid and liquid contaminants.

10. A apparatus as recited in claim 9, wherein said discharge apparatus comprises an oil container having a oil container lid at one end and a valve at the other.

11. A apparatus as recited in claim 10, wherein said oil container lid comprises:
    a) A oil line supported by a modular line hose and connected to a lid through a port connector;
    b) A vacuum source controlled by a valve connected to the lid through a vacuum port connector;
    c) A temperature measurement tester placed through a temperature measurement tester cavity on the lid.

12. A apparatus as recited in claim 9, wherein said separation and removal apparatus comprises:
    a) A magnetic contaminant separation and removal device placed above a non-magnetic particles separation and removal device;
    b) A non-magnetic contaminant separation and removal device connected to a liquid separation and removal device;
    c) A liquid separation and removal device connected to a fluid contaminant separated container.

13. A apparatus as recited in claim 12, wherein said magnetic contaminant separation and removal apparatus comprises:
    a) A contaminant density distribution ruler with a magnet and a black plate; a light source and a pivoted arm to support density ruler;
    b) A spout dispenser placed above the non-magnetic contaminant separation and removal apparatus.

14. A apparatus as recited in claim 12, wherein said non magnetic contaminant separation and removal apparatus comprises:
    a) a container with a drainage plug connected through a drainage line to a drainage container;
    b) A bypass filtration line with a valve connected to vacuum funnel;
    c) A vacuum funnel to support screen and to provide a vacuum port for vacuum line connected to vacuum source;
    d) A flask connector placed between a container and a fluid contaminant separator and removal apparatus.

15. A apparatus as recited in claim 12, wherein said liquid contaminants separation and removal apparatus comprises:
    a) A condensing container connected to a non-magnetic separation and removal apparatus through the flask connector;
    b) A chemical or mechanical means to separate fluid contaminant from oil connected to a contaminant fluid container;
    c) A flask container to keep the oil seperated from all contaminants.

16. A apparatus as recited in claim 9, wherein said separation and removal apparatus comprises:
    a) A magnetic contaminants separation and removal device;
    b) A non magnetic contaminants separation and removal device;
    c) A liquid contaminants separation and removal device.

17. A apparatus as recited in claim 16, wherein said magnetic and non magnetic contaminants removal apparatus comprises:

a) A printable surface with a adhesive side and a hole;
b) A filter with a diameter larger than a concentric hole and supported by a printable surface on one side and an adhesive surface on the other side;
c) A support mesh placed under the filter.

18. A apparatus as recited in claim 9, wherein said testing apparatus comprises:
 a) Testers selected from the group consisting of contaminant testers;
 b) Testers selected from the group consisting of oil testers.

19. A apparatus as recited in claim 18, wherein said contaminant testers comprises:
 a) Particle counter testers;
 b) Recorder and amplifiers of magnetic and non-magnetic contaminant images.

20. A apparatus as recited in claim 18, wherein said testers comprises of one or more of oil testers:
 a) Testers for TAN;
 b) Testers for TBN;
 c) Testers for color;
 d) Testers for opacity;
 e) Testers for chromatography;
 f) Testers for viscosity;
 g) Recorder and amplifiers of color and chromatography images.

21. A apparatus as recited in claim 20, wherein said testers for chromatography comprises:
 d) A printable surface with a adhesive side and a hole;
 e) A chromatography paper with a diameter larger than the concentric hole is supported by a printable surface on one side and an adhesive surface on the other side.

22. A apparatus as recited in claim 9, wherein tester apparatus further comprises a PC based analyzer which comprises:
 a) Interfacing cabling systems;
 b) Software apparatus to link all information for gathering, linking, relating and trending process and tester parameters and for recording images;
 c) LCD display.

* * * * *